United States Patent [19]

Miklavcic

[11] Patent Number: 5,111,495

[45] Date of Patent: May 5, 1992

[54] APPARATUS FOR REDUCTION OF SCATTER IN DIAGNOSTIC RADIOLOGY

[76] Inventor: Lucijan Miklavcic, Hrvatini 216a, Ankaran, Yugoslavia, YU-66280

[21] Appl. No.: 526,632

[22] Filed: May 22, 1990

[30] Foreign Application Priority Data

May 26, 1989 [YU] Yugoslavia ............................ 1095/89
Jun. 1, 1989 [YU] Yugoslavia ............................ 1133/89

[51] Int. Cl.$^5$ .......................... G21K 5/10; G21K 1/00
[52] U.S. Cl. ................................. 378/146; 378/154; 378/155; 250/505.1
[58] Field of Search ............... 378/146, 19, 151, 158, 378/145, 147, 148, 150, 152, 154, 155; 250/505.1

[56] References Cited

U.S. PATENT DOCUMENTS

| | | | |
|---|---|---|---|
| 4,096,391 | 6/1978 | Barnes | 378/146 |
| 4,264,824 | 4/1981 | Tosswill | 378/146 |
| 4,677,652 | 6/1987 | Duinker et al. | 378/146 |

*Primary Examiner*—Janice A. Howell
*Assistant Examiner*—Kim-Kwok Chu
*Attorney, Agent, or Firm*—Fleit, Jacobson, Cohn, Price, Holman & Stern

[57] ABSTRACT

Scanning slit radiography apparatus with a radiographic grid of the invention makes possible the X-ray imaging at an enhanced primary radiation transmission, yet at a reduced scatter transmission. By orienting long axes A of radiopaque strips 12 obliquely to the sweep S of the grid 1, the strips 12 being separated by air interspaces 13 can be performed with a sufficient own stiffness that no aluminum top and bottom covers are needed. The planes of downward lateral faces 12' intersect each other in an upward decentration line $D_+$ and the planes of upward lateral faces 12" intersect each other in a downward decentration line $D_-$. In a preferred embodiment of the invention the grid 1 is inclined during the sweep S so that the convergent line of the grid continues to pass through the tube focus.

1 Claim, 3 Drawing Sheets

APPARATUS FOR REDUCTION OF SCATTER IN DIAGNOSTIC RADIOLOGY

BACKGROUND OF THE INVENTION

1. Technical Field

This application relates generally to diagnostic X-ray medical imaging.

2. Description of the Prior Art

In the radiography, especially when performed with X-rays having the energy increasingly above 50 keV, which is used for medical diagnosing, the Compton scattering of the primary X-rays takes place with increasing probability. The direction of the propagation of secondary radiation, i.e. of scattered radiation, mainly differs from the direction of the propagation of primary X-radiation being emitted from the focal spot on the anode of the X-ray tube.

A scatter-removing radiographic grid placed between the object to be imaged and the cassette with the X-ray film prevents the secondary X-radiation from impinging on the film and thus from impairing the contrast of the X-ray image originating just from the primary X-radiation. The radiographic grid was protected by G. Bucky through U.S. Pat. No. 1,164,987. It is usually made of strips of a strongly absorbing metal as lead, i.e. of radiopaque strips, between which strips of a weakly absorbing substance as aluminum, i.e. radiolucent strips, are inserted. The long axes of the strips are mutually parallel, however, the strips are differently titled around these axes so that prolongated strip plains intersect themselves in a convergent line. During an exposure the radiographic grid oscillates within its plane transversely to its strips to prevent an imaging of the shadows of the radiopaque strips. Representative parameters of such radiographic grid are: 34 strip pairs/cm; the thickness of the aluminum strips is 0.25 mm and of the lead strips 0.05 mm; the ratio of the grid is 10; the grid is stiffened by an aluminum support cover of a thickness of 0.25 mm on its top and bottom; the transmission of the grid is 60% and its focal length, i.e. the distance of the convergent line from the grid, equals 1500 mm. It is a disadvantage of such radiographic grids that their transmission for the primary X-radiation is low and lies between about 60% and 65%; therefore the patient is exposed to a rather high dose of X-radiation. Furthermore, at the passage of the primary X-radiation across aluminum strips and support covers, the low energy X-radiation is absorbed at a higher rate, whereby the contrast of the X-ray image is impaired. Still another disadvantage of the radiographic grids known in the state of the art exists in that the radiopaque strips are thin and therefore rather translucent for the secondary X-radiation.

In the scanning slit radiography, however, the secondary X-radiation is eliminated by an aft slit, which is swept between the object to be imaged and the cassette with the X-ray film in synchrony with a beam defining the fore slit. The images are excellent. However, either the sweep of the fore and aft slit is slow causing an undesiredly long exposure time during which the patient might move or the X-radiation flux density is high, which requires a high X-ray tube loading. When wide body organs or regions, e.g. the chest, are imaged, the width of the aft slit must be increased in order to reduce the exposure time. It is a consequence thereof that the X-ray scatter impinges on the film, which impairs the quality of the image.

SUMMARY OF THE INVENTION

In accordance with the foregoing background discussion, the object of this invention is to provide a scanning slit radiography apparatus with a radiographic grid, which will make possible X-ray imaging with reduced transmission of scattered X-radiation at an enhanced transmission of primary X-ray radiation and with eliminated imaging of the radiopaque strips of the radiographic grid.

With the foregoing objects in view, the scanning slit radiography apparatus with a radiographic grid in accordance with the invention is characterized by features of the characterizing portion of claims 1 and 2 in the case of the first embodiment and of claims 1, 3 and 4 in the case of the second embodiment.

The construction of the radiographic grid in the scanning slit radiography apparatus proposed by the invention completely prevents the imaging of the grid strips together with as high a reduction of the filtration of the primary X-radiation as possible. By orienting the long axes of the strips within the grid obliquely to the sweep, the strips can be performed with an adequate transverse extension and their own stiffness is such that between them air interspaces are possible and no aluminum top and bottom support cover are needed. Thus the patient's exposure to radiation is reduced since the transmission of such grid for the primary X-radiation is high. Because of the weak filtration of this radiation, the portion of the low energy X-radiation in the imaging beam is nearly intact, which has a favourable effect upon the contrast of the image. Another advantage exists in that the construction of the grid allows a greater height of the radiopaque strips and thereby a more complete suppression of the scatter at the area of the X-ray film.

The transmission of the radiographic grid, which during the sweep also changes its inclination so that the convergent line of the grid during the whole sweep passes through the focus of the X-ray tube, is higher than the one of the grid being swept in the known translatory way, since in this preferred embodiment of the invention the cross section of the radiopaque strips can be changed from a nearly triangular form with an extensive base line to a more pronounced trapezium form with a smaller difference between the length of the base line and the thickness of the strip at its top or even to a rectangular form.

Other objects, advantages and features of the invention will be apparent from the following detailed description of both embodiments thereof, when read in conjunction with the accompanying drawings.

DETAILED DESCRIPTION OF THE PREFERRED EMBODIMENT

Figure 1:
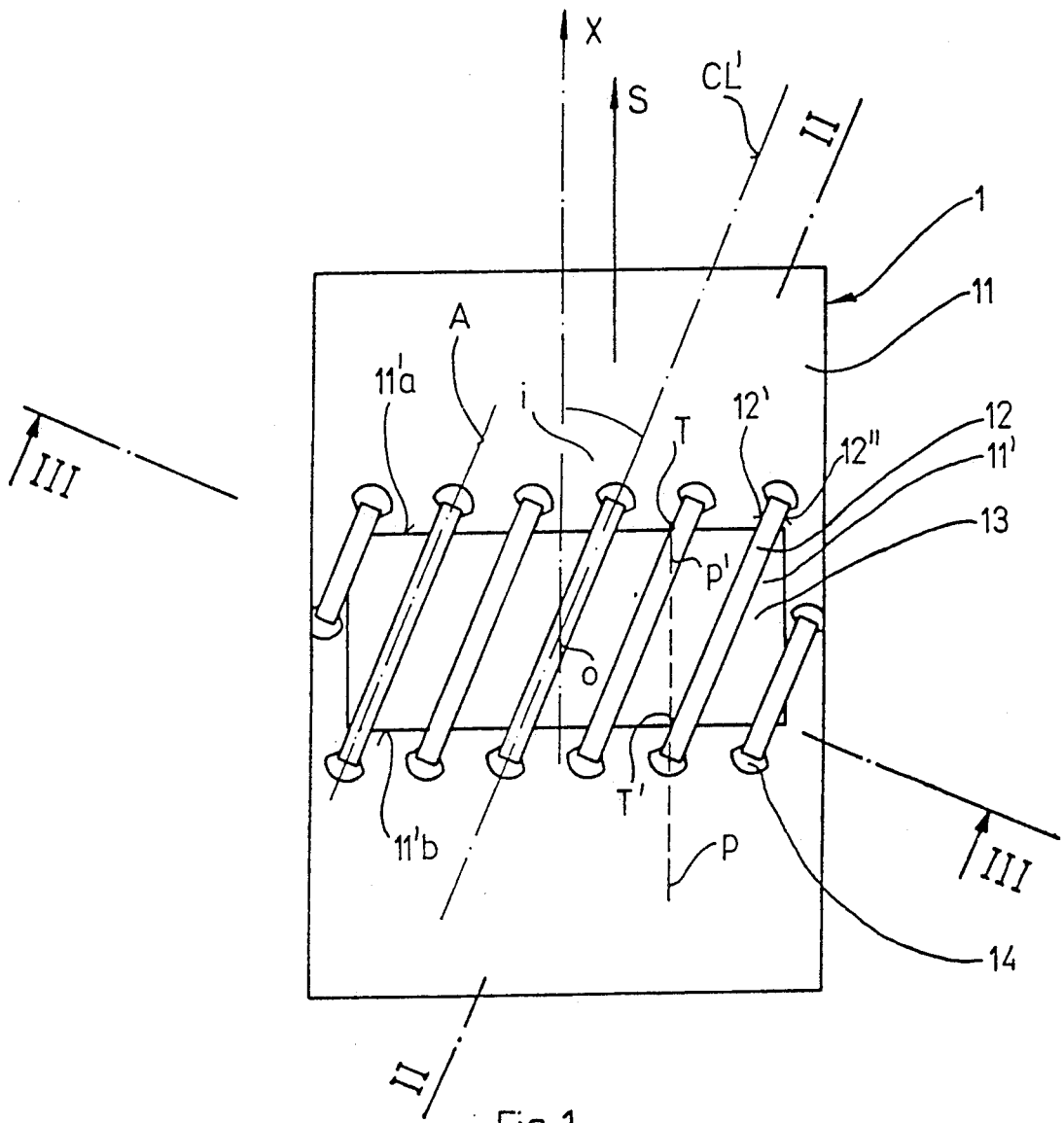
FIG. 1 is a top view of the construction of the radiographic grid in the scanning slit radiography apparatus of the invention.
Figure 3:
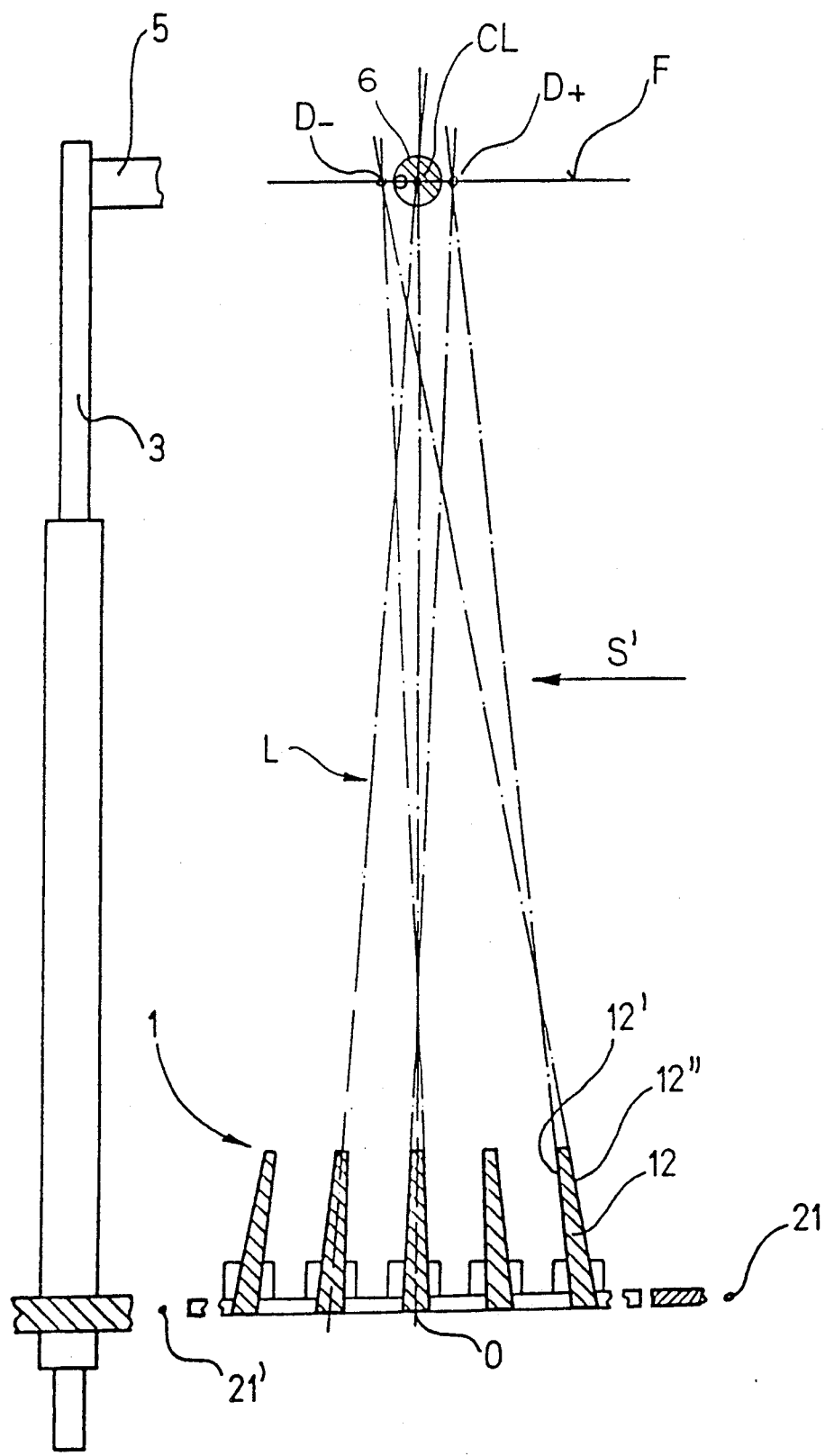
FIG. 3 is the cross section of the radiographic grid across the line III—III in FIG. 1.
Figure 4:
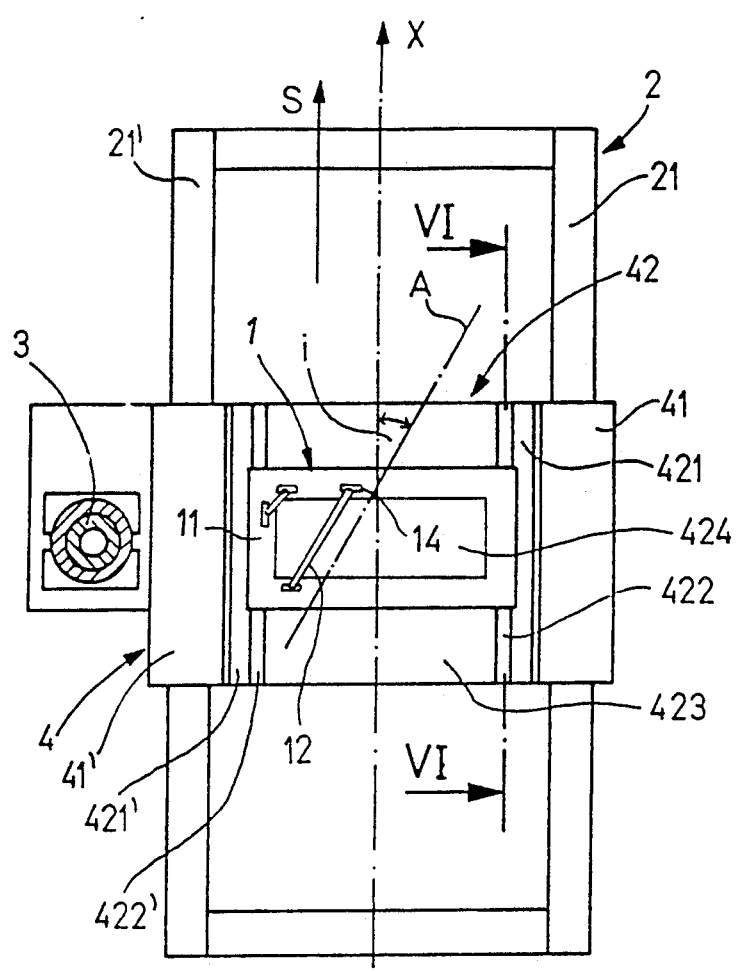
FIG. 4 is a top view of the scanning slit radiography apparatus with the radiographic grid.

A top view of a radiographic grid 1 in the scanning slit radiography apparatus of the invention is shown in FIG. 1. A radiopaque frame 11 of the grid 1 is mounted in a carriage 4, which is sweepable along guide bars 21, 21' of a sweeping guide frame 2 (FIG. 4). During the X-ray exposure the carriage 4 performs a sweep S. The guiding frame 2 is movably mounted to a transversal guide bar 3, to which a bar 5 carrying an X-ray tube 6 and a collimator (not shown) is fastened (FIG. 3). Generally speaking, in each instant the longitudinal axis X of the grid 1 is parallel to the sweep S. In the frame 11 a rectangular aperture 11' is performed. The downward border 11'a and the upward border 11'b, with respect to the sweep S, of the aperture 11' are normal to the axis X.

Figure 2:
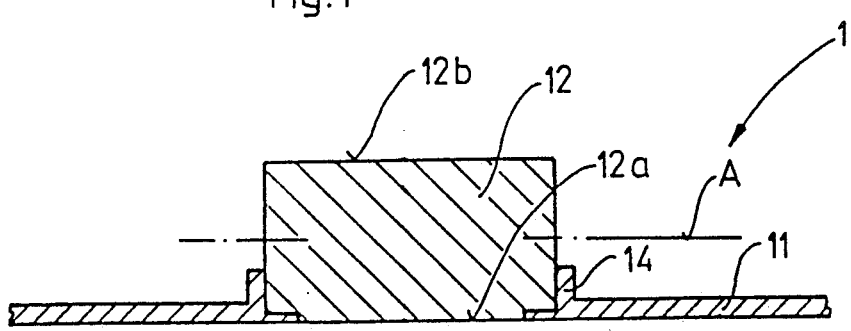
FIG. 2 is the cross section of the radiographic grid across the line II—II in FIG. 1.

Radiopaque strips 12 are fastened to the grid frame 11 by means of fasteners 14 (FIGS. 1 and 2). By the radiopaque strips 12 the aperture 11' is separated into air interspaces 13. The long axes A of the strips 12 are mutually parallel. The strips 12, however, are tilted around the axes A differently so that the median planes L of the strips 12 intersect each other at a convergent line CL of the focal plane F of the grid 1 (FIG. 3). A projection of the convergent line CL to the plane of the grid 1 is labelled by CL'. The point of intersection of the projection CL' with the grid axis X is situated in the middle point O of the grid 1 (FIG. 1).

A downward lateral face 12' and an upward lateral face 12", with respect to the sweep S or, more precisely, with respect to a projection S' of the sweep S onto the plane of FIG. 3, of each strip 12 are inclined to the median plane L of the strip 12 so that the strip cross section is trapezial. The inclinations of the lateral faces 12', 12" are, however, such that the planes of the downward lateral faces 12' of all strips 12 intersect each other in an upward decentrated line $D_+$ and that the planes of the upward lateral faces 12" of all strips 12 intersect each other in a downward decentrated line $D_-$. The decentrated lines $D_-$, $D_+$ are situated in the focal plane F of the grid 1.

The strips 12 are fastened to the frame 11, as shown in FIG. 1, so that the angle i between their axes A and the axis X is defined as follows. The point T of intersection of the downward border 11'a with the downward lateral face 12' of any strip 12 is situated on the same line p, which is parallel to the axis X, as the point T' of intersection of the upward border 11'b with the downward lateral face 12' of the next strip, which is situated upwardly with respect to the former strip 12. Consequently, the points T, T' of intersection are equidistant from the axis X. Therefore, a total length p' of the line p within one or at most two next strips is the same for any line p at an arbitrary distance from the axis X. This condition must be fullfilled for both extreme strips 12 as well.

Figure 5:
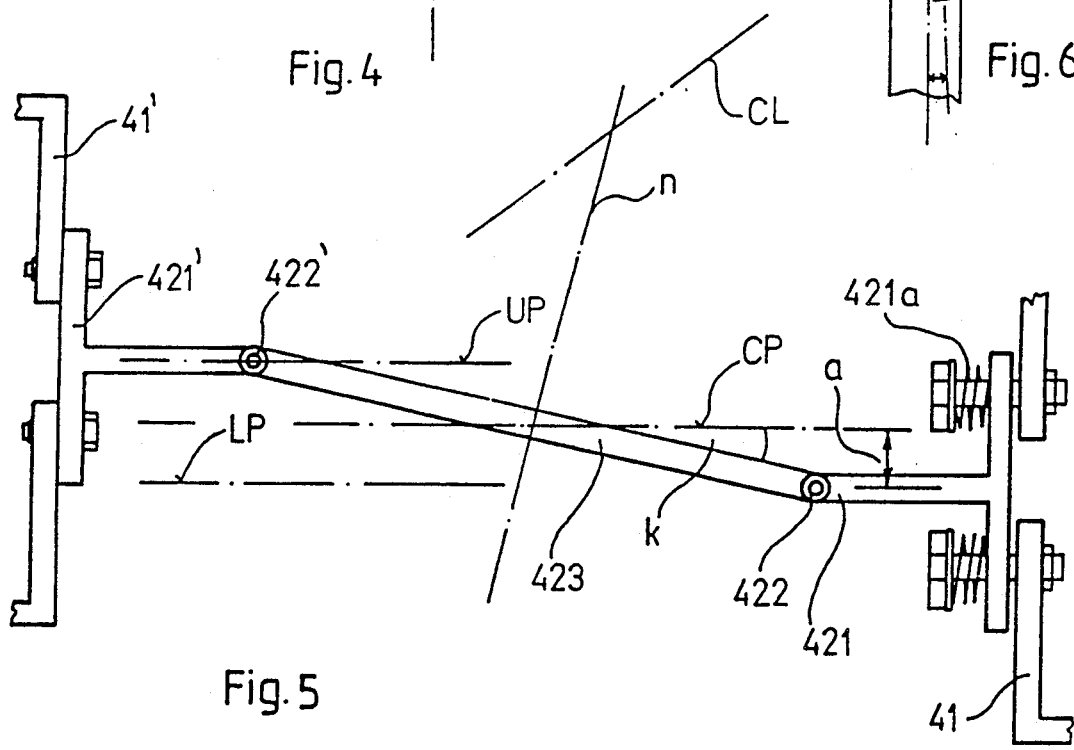
FIG. 5 is a view in the direction of the sweep of the carriage and partially of a sweep guide within the apparatus of the invention.

The guide bars 21, 21' of the guide frame 2 are mutually parallel or, according to the preferred embodiment of the invention, mutually skewed for a small angle 2j. The carriage 4 consists of a holding frame 42 provided to receive the radiographic grid 1 and of sliding shells 41, 41'. The sliding shells 41, 40' are mounted on the guide bars 21, 21' so that they can translatorily sweep along them. In the preferred embodiment, however, uninclinable frame pieces 421, 421' are fastened to the sliding shells 41, 41'. An inclinable frame piece 423, which is provided with a central opening 424 to receive the radiographic grid 1, is pivotally attached to the uninclinable frame pieces 421, 421' by means of hinges (422, 422', resp.) (FIGS. 4 and 5).

Figure 6:
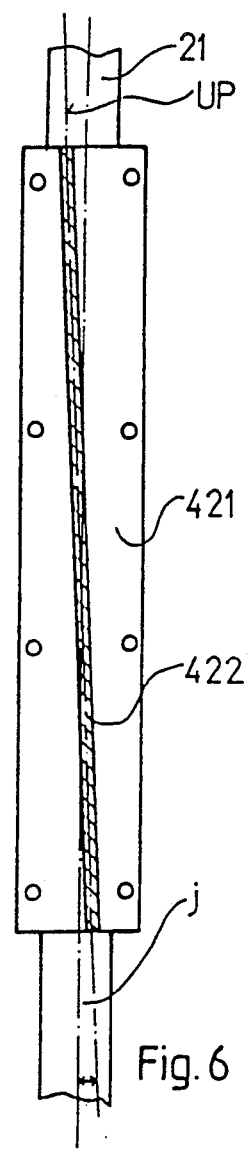
FIG. 6 is the cross section of the carriage across the line VI—VI in FIG. 4.

The projections of the guide bars 21, 21' onto the plane CP of the uninclinable piece 423, i.e. of the grid 1, in the middle of the sweep S are mutually parallel. With respect to the plane CP the guide bar 21 rises at the angle j, and the guide bar 21' descends at the angle j (FIG. 6). Hence the axes of the hinges 422, 422' being situated in the plane of the inclinable frame piece 423 are inclined at the angles $+j$ and $-j$, respectively, with respect to the guide bars 21, 21'. In a small angle approximation the angle $2j$ of the mutual skewness of the guide bars 21, 21' is determined by the focal length f of the radiographic grid 1, by the grid decentration e, by the distance w between the hinges 422, 422' and by the length s of the sweep S:

$$2j = (e^*w)/(f^*s).$$

In the embodiment of the apparatus of the invention with mutually parallel guide bars 21, shown in FIG. 4 21', the radiographic grid 1, e.g. provided for the imaging of a complete spinal column onto a film of dimensions 30 cm × 90 cm, has the following design parameters. The aperture 11' of the grid frame 11 determines an X-radiation beam of a height of 150 mm as determined by the distance between the borders 11'a, 11'b and of a width of 300 mm. The sweep length s is 1050 mm. The radiopaque strips 12 of a height (h) of 24 mm are made of tantalum; they have a thickness of 0.50 mm at the base line 12a and a thickness of 0.28 mm at top edge 12b. The width D of the air interspaces 13 at the level of the strip base lines 12a is 2.00 mm. The angle i between the strip axes A and the grid axis X is determined by sin i = 1/60. The ratio h/D of the grid 1 is 12. The primary X-radiation transmission is as high as 80%.

By moving the carriage 4 along the transversal guide bar 3, the focal plane F of the radiographic grid 1 is positioned to include the focus of the X-ray tube. Further, in the middle of the sweep S the middle point O of the grid 1 must be situated just below the focus of the X-ray tube, i.e. the focus will be on the convergent line CL at that moment. In the middle of the sweep S the maximum transmission of the grid 1 is achieved by the convergence of the median planes L of the strips 12 towards the convergent line CL, at both extreme positions, however, this is accomplished by such an additional inclination of the lateral faces 12', 12" of the strips 12 that the planes of the lateral faces converge towards decentrated lines $D_+$ and $D_-$ as shown in FIG. 3. The lines $D_-$, $D_+$ are determined so that at the extreme upward position of the sweep S the tube focus is situated on the downward decentrated line $D_-$ of the grid 1, and that at the extreme downward position of the sweep S the tube focus is situated on the upward decentrated line $D_+$ of the grid 1. Thereby it is prevented that the upper strip portion would filter the X-ray radiation which would otherwise most probably only pass a part of the strip height h, i.e. a part of the distance between the strip base line 12a and the strip upper edge 12b. An extremely exact blurring out of the image of the grid strips 12 is accomplished by the above defined inclination angle i of strip axis A with respect to the grid axis X. Thus the angle i depends on the X-radiation beam height H, which equals the mutual distance of the borders 11'a and 11'b of the grid aperture 11'. By the radiographic grid 1 proposed by the invention an excellent diagnostic quality of the images of a human spinal column can be achieved also at high anode voltages ranging from 90 to 100 kV. Thereby the dose absorbed by the patient is reduced to $\frac{1}{3}$ to $\frac{1}{4}$ of the dose that is absorbed when a patient is imaged with a known Pb/Al grid at the anode voltages of 60 to 70 kV. This reduction of the absorbed dose is a consequence of the above indicated advantages of the grid proposed by the invention and of a higher sensitivity of the film-screen combination at this anode voltage.

The preferred embodiment of the apparatus of the invention with mutually skewed guide bars 21, 21' functions as follows. When the carriage 4 performs the sweep S, the uninclinable frame piece 421, 421' translatorily rises or descends, respectively, between the lower plane LP and the upper plane UP, which are separated by a distance 2a. In the middle of the sweep S the uninclinable frame pieces 421, 421' are in the same plane CP as there is also the inclinable frame piece 423 with the radiographic grid 1. In this position a normal to the radiographic grid 1 through its middle point O passes through the focus of the X-ray tube. When the carriage 4 is sweeped for the length s of the sweep S, the inclinable frame piece 423 and thereby the radiographic grid 1 is inclined by rotation around the grid axis X by an angle 2k. During the sweep S the convergent line CL of the radiographic grid 1 moves so that it continues to pass through the X-ray tube focus. As the radiographic grid 1 inclines around the axis X during the sweep S, each point of the convergent line CL draws an arc of a length equal to the decentration e of the grid; during the imaging the radiographic grid 1 is continuously centered, which makes possible a still more favourable shaping of the cross section of its radiopaque strips 12. Since in each instant the direction of the sweep S coincides with the axis X of the grid 1, the imaging of the strips 12 is completely prevented.

The design parameters of the preferred embodiment of the apparatus of the invention are as follows. For the X-ray imaging on a film 435 mm × 435 mm the height h of the radiopaque strips 12 is 30 mm. The width d of the base line 12a is 0.50 mm and the width D of the air interspace 13 at the base line level is 2.50 mm. The distance H between the downward and the upward borders 11'a, 11'b of the grid aperture 11', i.e. the dimension of the X-ray beam in the direction of the sweep S, is 50 mm and the transverse dimension w of the grid aperture 11' is 435 mm. The grid ratio h/D equals 12, the transmission of the grid for the primary X-radiation is 83%. For the imaging on the film of the above dimensions the decentration $e=(w/h+1)(D+d)=29.10$ mm is required. Hence the angle of mutual skewness of the guiding bars 21, 21' equals 1°. Therefore the radiographic grid 1 in a complete sweep S is inclined for the angle $2k=1°$. The uninclinable frame piece 421 is connected to the sliding shell 41 by a spring 421a to compensate its tiny displacement transversely to the chord of the length 2a corresponding to the central angle $2k=1°$.

What is claimed is:

1. A scanning slit radiography apparatus with a radiographic grid, of radiopaque strips a radiopaque frame of the grid being mounted on a carriage, which is sweepable along guide bars of a sweeping guide frame so that the grid in each instant is moved along its longitudinal axis, and a rectangular aperture made in the radiopaque frame and having a downward border and an upward border, with regard to the direction of the sweep being performed in the radiopaque frame, whereby the borders are normal to the longitudinal axis, characterized in that downward lateral faces of each two next radiopaque strips, which are fastened to the radiopaque frame and traverse the aperture with mutually parallel long axes, cut opposite borders at points which are equidistant from the longitudinal axis, and that the strips, whose long medial planes intersect each other in a convergent line, are shaped in such manner that planes of the downward lateral faces intersect each other in an upward decentrated line and planes of upward lateral faces intersect each other in a downward decentrated line.

2. An apparatus as recited in claim 1, characterized in that the guide bars are mutually parallel.

3. An apparatus as recited in claim 1, characterized in that the guide bars are mutually skewed for such an angle 2j, where j is the angle at which the guide bar rises, that the convergent line of the radiopaque grid passes through the focus of the X-ray tube of the apparatus during the entire duration of the sweep, the projections of the guide bars onto the plane of the grid in the middle of the sweep being mutually parallel.

4. An apparatus as recited in claim 3, characterized in that the carriage comprises a sliding shell and an uninclinable framepiece in which the sliding shell of the carriage is mounted to the guide bar sweepably and uninclinably, that the uninclinable frame piece of the carriage is fastened to the sliding shell, and that an inclinable frame piece which is provided with a central opening to receive the grid, is pivotally attached to the uninclinable frame pieces by means of hinges being displaced by the angle +j, −j, respectively, with respect to the guide bars.

* * * * *